United States Patent [19]
Adolph et al.

[11] Patent Number: 4,740,628
[45] Date of Patent: Apr. 26, 1988

[54] 2,4,4,5,5,6,6-HEPTAFLUORO-2-TRI-FLUOROMETHYL-3-OXAHEPTANE-1,7-DIOL POLYFORMAL AND METHOD OF PREPARATION

[75] Inventors: Horst D. Adolph; Judah M. Goldwasser, both of Silver Springs, Md.

[73] Assignee: The United States of America as represented by the Secretary of the Navy, Washington, D.C.

[21] Appl. No.: 52,501

[22] Filed: May 5, 1987

[51] Int. Cl.$^4$ ............... C07L 43/30; C07L 43/313
[52] U.S. Cl. ............... 568/603; 568/601; 568/604; 528/76
[58] Field of Search ............... 568/601, 603, 604

[56] References Cited

U.S. PATENT DOCUMENTS 3,419,531 12/1968 Trischler ............... 568/601

Primary Examiner—Howard T. Mars
Attorney, Agent, or Firm—Kenneth E. Walden; Roger D. Johnson

[57] ABSTRACT

2,4,4,5,5,6,6-heptafluoro-2-trifluoromethyl-3-oxaheptane-1,7-diol polyformal, $HOCH_2CF_2CF_2CF_2OCF(CF_3)CH_2O[CH_2OCH_2CF_2CF_2CF_2OCF(CF_3)CH_2O]_nH$, which is prepared by reacting the diol with formaldehyde in 80–90 percent sulfuric acid.

2 Claims, No Drawings

2,4,4,5,5,6,6-HEPTAFLUORO-2-TRI-FLUOROMETHYL-3-OXAHEPTANE-1,7-DIOL POLYFORMAL AND METHOD OF PREPARATION

BACKGROUND OF THE INVENTION

This invention relates to fluoropolymers and more particularly to curable polyfluoro prepolymers.

Fluoropolymers are used as binders in high-density explosives and propellants and in energetic compositions requiring a high degree of thermal stability. For example, fluoropolymers are used extensively in such compositions which are pressed. However, very few fluoropolymers exist which have functional groups such as hydroxy which are suitable for curing and thus can be used as binders in castable or extrudable compositions. Two known examples of such polymers are the fluoropolyethers FC2202 and L9019 made by the 3M Company. While useful for some purposes, these polymers are expensive and completely fluorinated. The absence of hydrogen limits the compatibility of these polymers with conventional plasticizers, curing agents, and other polymers.

SUMMARY OF THE INVENTION

Accordingly, a object of this invention is to provide a new curable polyfluoro prepolymer.

Another object of this invention is to provide a new curable polyfluoro prepolymer which is miscible with conventional plasticizers, curing agents, and other polymers.

A further object of this invention is to provide a curable polyfluoro prepolymer which may be used to provide a binder in castable or extrudable composites.

Still another object of this invention is to provide an energetic, curable prepolymer for use in a binder in castable or extrudable explosive or propellant compositions.

These and other objects of this invention are accomplished by providing1 2,4,4,5,5,6,6-heptafluoro-2-trifluoromethyl-3-oxaheptane-1,7-diol polyformal, $HOCH_2CF_2CF_2CF_2OCF(CF_3)CH_2O[C-H_2OCH_2CF_2CF_2CF_2OCF(CF_3)CH_2O]_nH$, wherein $n>1$, which is prepared by reacting 2,4,4,5,5,6,6-heptafluoro-2-trifluoromethyl-3-oxaheptane-1,7-diol with formaldehyde in 80–90% sulfuric acid.

DETAILED DESCRIPTION OF THE PREFERRED EMBODIMENT 2,4,4,5,5,6,6-Heptafluoro-2-trifluoromethyl-3-oxaheptane-1,7-diol polyformal, $HOCH_2CF_2CF_2CF_2OCF(CF_3)CH_2O[C-H_2OCH_2CF_2CF_2CF_2OCF(CF_3)CH_2O]_nH$, is a thermally stable, hydroxy-terminated polymer which is suitable for use in binders for energetic explosive and propellant compositions. The polymer preferably have a number average molecular weight of from 1,500 to 10,000 and more preferably from 2000 to 4000. In the number average molecular weight range of 2000 to 4000, 2,4,4,5,5,6,6-heptafluoro-2-trifluoromethyl-3-oxaheptane-1,7-diol polyformal, is a viscous oil having a density of about 1.73 g/cm³.

In addition to being soluble in highly fluorinated and perfluoronated solvents, 2,4,4,5,5,6,6-heptafluoro-2-trifluoromethyl-3-oxaheptane-1,7-diol polyformal is soluble in non-fluorinated organic solvents and compounds. For example, this polymer is soluble in ether, tetrahydrofuran, bis(2-fluoro-2,2-dinitroethyl)formal (FEFO), 2,2,2-trifluoroethoxy bis(2-fluoro-2,2-dinitroethoxy)methane (trifluoroethoxy-FEFO). This solubility property provides flexibility in formulating binder compositions and it also makes 2,4,4,5,5,6,6-heptafluoro-2-trifluoromethyl-3-oxaheptane-1,7-diol polyformal useful as a block for preparing block-copolymers with non-fluorinated polymers such as polyethylene glycol or poly(4,4-dinitroheptane-1,4-diol). 2,4,4,5,5,6,6-heptafluoro-2-trifluoromethyl-3-oxaheptane-1,7-diol polyformal is dihydroxy-terminated and may be cured by conventional means such as commercially available polyisocyanates.

2,4,4,5,5,6,6-heptafluoro-2-trifluoromethyl-3-oxaheptane-1,7-diol polyformal can be prepared in approximately 75 percent yield by reacting 2,4,4,5,5,6,6-heptafluoro-2-trifluoromethyl-3-oxaheptane-1,7-diol with formaldehyde and 80–90 percent (W/W) sulfuric acid as described in examples 1 and 2. The molecular weight of the polymer product can be controlled by adjusting the diol to formaldehyde ratio, the amount and concentration of sulfuric acid used, and the quantity of organic solvent present during the reaction.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1 2,4,4,5,5,6,6,-Hetafluoro-2-trifluoromethyl-3-oxaheptane-1,7-diol polyformal In a 1L 3-neck flask 146.1 g (0.445 mole) of 2,4,4,5,5,6,6-heptafluoro-2-trifluormethyl-3-oxaheptane-1,7-diol and 90.0 mL of 80 percent (w/w) $H_2SO_4$ were mixed under a $N_2$ blanket until homogeneous. The mixture was cooled in an ice-bath and 117 mL of dry dichloromethane was added. To the vigorously stirred mixture, a solution of 10.8 g (0.360 mol) of paraformaldehyde in 63 mL 90 percent sulfuric acid (w/w) was added with continued cooling, and then the mixture was stirred for 20 hours at room temperature. The reaction mixture was poured over ice. 900 mL of ether and 90 mL of 30 percent $H_2O_2$ was added, and the mixture was stirred vigorously for one hour. The organic layer was washed thoroughly with 675 mL of 5 percent aqueous KOH+45 mL of 30 percent $H_2O_2$ then with 675 mL of brine. After drying ($CaSO_4$), the solution was filtered through a medium porosity sinterglass funnel and freed of solvents in vacuo. The resulting polymer was heated overnight at 120° C., collecting volatiles in a trap immersed in an acetone-dry-ice bath. The yield of 2,4,4,5,5,6,6-heptafluoro-2-trifluoromethyl-3-oxaheptane-1,7-diol polyformal polymer was 113 g (74.6%). $M_n=2770$; $M_w=5147$; $M_w/M_n=1.86$. The dry-ice trap contained 35.7 g of mostly unreacted diol; based on reacted diol, the polymer yield was 98 percent.

EXAMPLE 2

2,4,4,5,5,6,6-heptafluoro-2-trifluoromethyl-3-oxaheptane-1,7-diol polyformal

In a 50 mL 3-neck flask, 9.74 g (0.0297 mol) 2,4,4,5,5,6,6-heptafluoromethyl-3-oxaheptane-1,7-diol and 13 mL of dry (4 Å sieves) dichloromethane were mixed under a $N_2$ blanket. With cooling in an ice-bath and vigorous stirring, a solution of 0.846 g paraformaldehyde in 4.4 mL of 90 percent sulfuric acid was added dropwise. The mixture was allowed to warm to room temperature and was stirred for 20 hours at room temperature. The reaction mixture was quenched on ice, 60 mL of 30 percent $H_2O_2$ were added and the whole was stirred vigorously for 1 hour. The organic phase was separated and washed with 45 mL of 5 percent aqueous KOH and 3 mL of 30 percent $H_2O_2$, then with 45 mL of brine. The polymer solution was dried over 4 Å molecular sieves and was passed through a short column (2"×1") of Silica gel. After removal of the solvent, the polymer was heated 8 hours at 130° C./0.5 torr to remove volatiles. Obtained was 7.76 g of 2,4,4,5,5,6,6-heptafluoro-2-trifluoromethyl-3-oxaheptane-1,7-diol polyformal (76.8 percent). $M_n=3174$; $M_w=5490$; $M_w/M_n=1.73$. 2.4 g of volatile material was collected during heating; this was mostly unreacted 2,4,4,5,5,6,6-heptafluoro-2-trifluoromethyl-3-oxaheptane-1,7-diol.

The 2,4,4,5,5,6,6-heptafluoro-2-trifluoromethyl-oxaheptane-1,7-diol used in this invention is available from the 3M Corporation, St. Paul, Minnesota, which produces it on a semicommercial basis using a proprietary process.

EXAMPLE 3

2 g of the 2,4,4,5,5,6,6-heptafluoro-2-trifluoromethyl-3-oxaheptane-1,7-diol polyformal prepared in example 2 was mixed with 1 g of Fluorolube and the mixture was warmed until homogeneous. Then 0.108 g of isophorone diisocyanate (IPDI, equiv. wt. 111) and 0.072 g isophorone diisocyanate trimer (IPDI-T, equiv. wt. 294) were added and the mixture was stirred until homogeneous. The mixture was then degassed for 30 minutes at 60° C. under vacuum. Curing was achieved without a catalyst by heating to 60° C. for one week. A gumstock with excellent elongation and strong adhesive properties was obtained.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. 2,4,4,5,5,6,6-heptafluoro-2-trifluoromethyl-3-oxaheptane-1,7-diol polyformal, having the formula $HOCH_2CF_2CF_2CF_2OCF(CF_3)CH_2O[CH_2OCH_2CF_2CF_2CF_2OCF(CF_3)CH_2O]_nH$, wherein $n>1$, having a number average molecular weight of from about 1500 to about 10,000.

2. The polyformal of claim 1 having a number average molecular weight of from 2000 to 4000.

* * * * *